United States Patent [19]

Boucher

[11] 4,211,744

[45] Jul. 8, 1980

[54] PROCESS FOR ULTRASONIC PASTEURIZATION

[75] Inventor: Raymond M. G. Boucher, New York, N.Y.

[73] Assignee: Biophysics Research & Consulting Corporation, New York, N.Y.

[21] Appl. No.: 908,964

[22] Filed: May 24, 1978

[51] Int. Cl.² ............................................. A61L 1/00
[52] U.S. Cl. .................................................. 422/20
[58] Field of Search ............................ 134/1; 422/20

[56] References Cited

U.S. PATENT DOCUMENTS

| 2,510,796 | 6/1950 | Brown | 422/20 X |
| 2,814,575 | 11/1957 | Lange | 134/1 |
| 2,970,073 | 1/1961 | Prange | 134/1 |
| 2,994,330 | 8/1961 | Catlin et al. | 134/1 X |
| 3,007,478 | 11/1961 | Leonhardt et al. | 134/1 X |
| 3,033,710 | 5/1962 | Hightower et al. | 134/1 |
| 3,034,520 | 5/1962 | Jewell | 134/1 X |
| 3,291,640 | 12/1966 | Livingston | 134/1 |
| 3,402,075 | 9/1968 | Goldwasser et al. | 134/1 |
| 3,403,245 | 9/1968 | Eaton | 134/1 X |
| 3,481,687 | 12/1969 | Fishman | 134/1 X |
| 3,516,861 | 6/1970 | Menkes et al. | 134/1 |
| 3,640,295 | 2/1972 | Peterson | 134/1 X |
| 3,672,823 | 6/1972 | Boucher | 134/1 X |
| 3,708,263 | 1/1973 | Boucher | 422/20 |
| 3,912,450 | 10/1975 | Boucher | 422/20 |
| 3,990,906 | 11/1976 | Johnston et al. | 134/1 |

FOREIGN PATENT DOCUMENTS 947699  1/1964  United Kingdom .................... 422/20

OTHER PUBLICATIONS

Bulat, T. V., "The Present State-of-The-Art in Sonic Cleaning", J. Amer. Assoc. Contamination Control, 10/65, pp. 22-24.

Primary Examiner—Barry S. Richman
Attorney, Agent, or Firm—Shoemaker and Mattare, Ltd.

[57] ABSTRACT

A method for pasteurizing, decontaminating or disinfecting the surfaces of medical, dental, surgical, and food processing instruments or other objects in a liquid phase by placing said objects in hot water or a hot aqueous solution whose temperature is between about 48° C. and 68° C. while irradiating at the same time the liquid and objects with an ultrasonic cavitating field whose main frequency is lower than 150 KHz and the average acoustic energy density greater than 5 watts per liter. According to acoustic intensity and temperature, the ultrasonic pasteurizng time may vary from 15 to 30 minutes. The method is compatible with the use of surfactants and detergents of the anionic, non-ionic, cationic and amphoteric type and can be performed in either a continuous or batch process.

10 Claims, 2 Drawing Figures

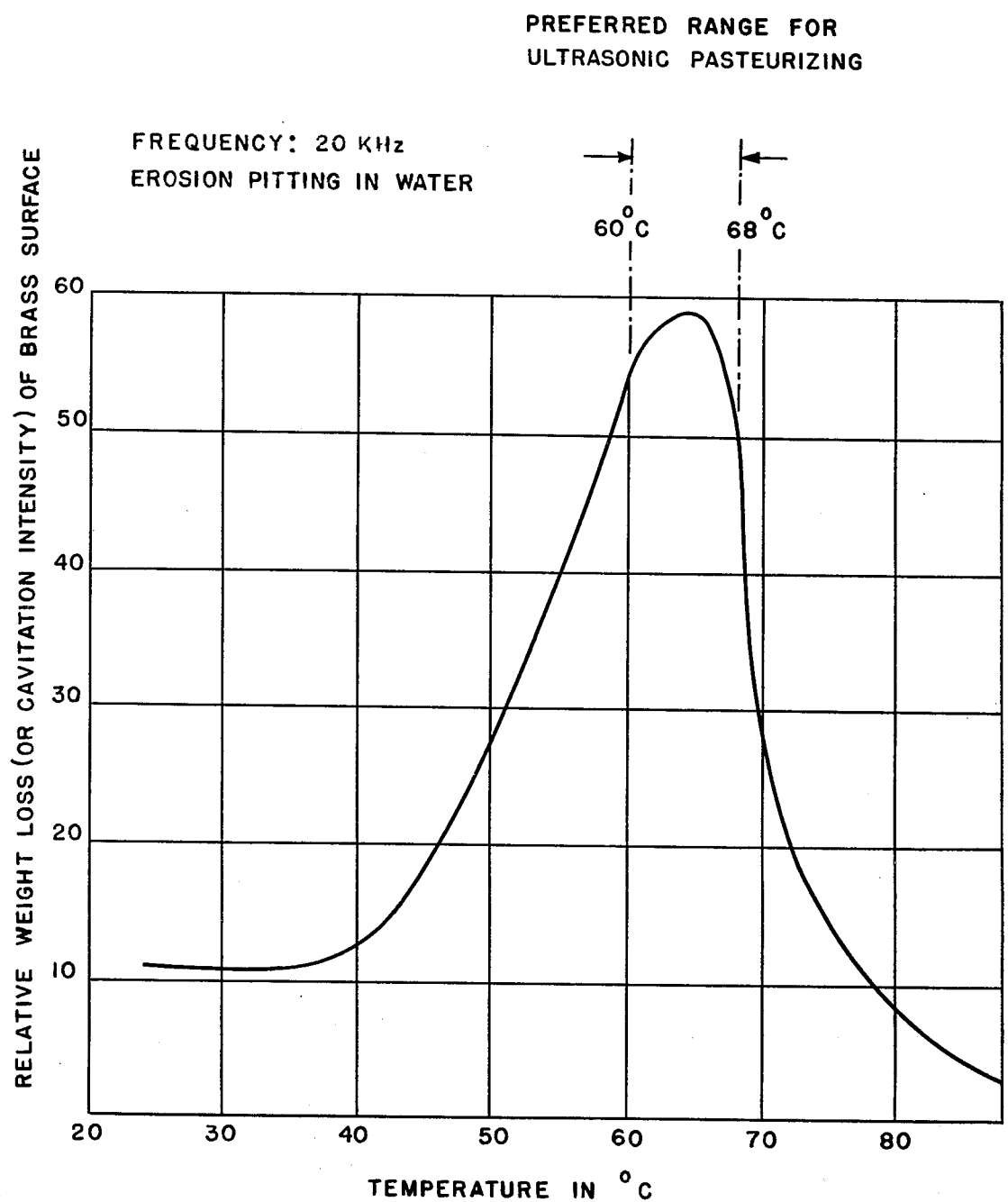

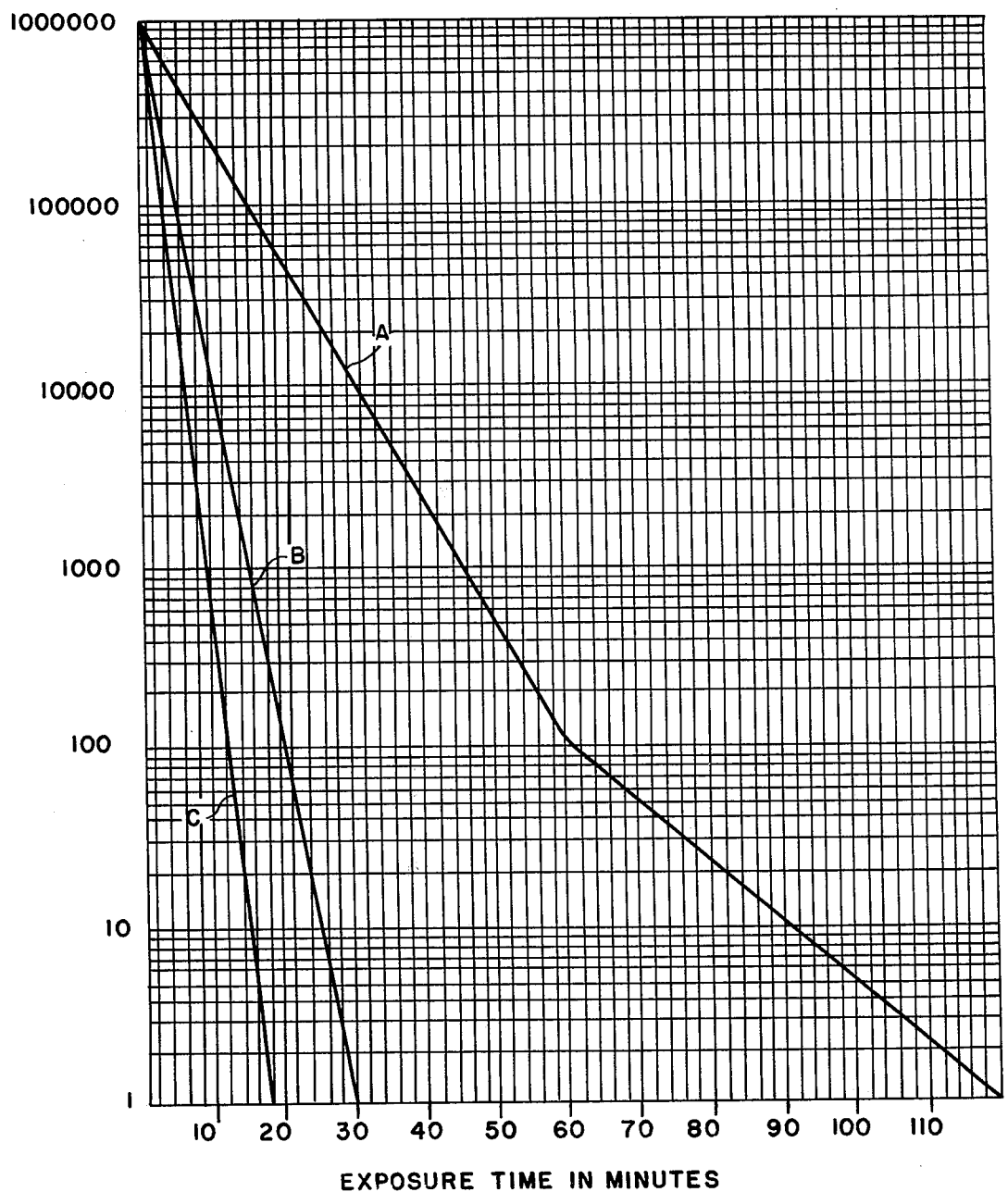

PROCESS FOR ULTRASONIC PASTEURIZATION

BACKGROUND OF THE INVENTION

1. Field of the Invention

This invention relates to a process of ultrasonic pasteurization wherein, the time and temperature needed to kill non-sporulated bacteria, vegetative cells fungi and viruses, on contaminated surfaces, is reduced.

More specifically, it deals with liquid phase pasteurization in either heated water or aqueous liquids wherein objects to be pasteurized are placed and irradiated with an ultrasonic field below 150 KHz and an average acoustic energy density greater than 5 watts per liter for from 15 to 30 minutes.

2. Description of the Prior Art

In food science, pasteurization is defined as a heat treatment that kills part but not all of the vegetative microorganisms present in the food and, consequently, is used for foods which are further handled and stored under conditions which minimize growth (i.e., refrigeration). However, in some cases (milk, for instance) pasteurization corresponds to the complete destruction of all pathogenic microorganisms. Minimum legal time-temperature relationships have been established for pasteurization of milk. These are (1) the low-temperature, long-time method (Holder process) in which every particle of milk is heated to 62.8° C. and held at that temperature for 30 minutes; and (2) the high-temperature, short-time method (H-T, S-T or "flash" process) involving an exposure of milk to 71.7° C. for 15 sec. Another method, that of ultra-high temperature (UHT) employs temperatures near 93.3° C. or above for a fraction of a second.

In world-wide practice, one or more of four general temperature zones are in use for heat-treating milk. These are (1) 62.8° C. for 30 min. and/or 71.7° C. for 15 sec.; (2) 79.4° C.–90.6° C. for 15 sec. or less; (3) 93.3° C.–100° C., and (4) above 107.2° C. momentarily up to 30 min.

When handling non-food material, the pasteurization method means, in general, the complete destruction of the various non-spore forming pathogens which can be encountered in each particular situation. One, therefore, must accurately define the type of microorganisms which may be encountered in a specific problem before claiming complete destruction of all non-spore formers by pasteurization. For instance, it has been shown that *Mycobacterium tuberculosis* has a thermal death point of 60° C. for 20 minutes, while *Staphylococcus aureus* has a thermal death point of 65.6° C. for 30 minutes.

It has recently been established that a satisfactory decontamination of anesthesia, resporatory therapy and urology equipment can be achieved by submerging said equipment into hot water during 30 minutes at a temperature of 76.7° C. (170° F.). This particular pasteurization or hot water disinfection technique is said to be based mainly on the coagulation and denaturization of the microorganism proteins.

Since the early thirties (Schmitt F. O., Uhlenmeyer B., The Mechanism of the Lethal Effect of Ultrasonic Radiation, Proc. Soc. Exptl. Biol. Med., 27:626–628, 1930), the cidal effects of ultrasonics on microorganisms suspended in liquid media has been well-recognized. The ultrasonic approach has been widely used both at laboratory and industrial scale to kill microorganisms, disrupt them or extract valuable compounds (enzymes, etc.). Theory and practice have both shown that lethal effects are a function of cavitation intensity and this is why, today, all large scale industrial processing applications are confined to the frequencies below 150 KHz.

In a cavitating field, microorganisms are submitted to the large amplitude shock waves released after the collapse of vapor filled resonant bubbles. These shock waves disrupt agglomerates and damage the protective membrane of microorganisms. They can physically break large molecules or viruses into smaller entities. Essentially, the same mechanism is used in cleaning applications. In this case, the pressure shock waves clean the surface of a material by jarring or knocking the scale or dirt from the surface. If exposing a metal over extended periods of time in a low frequency cavitating field, "pitting" will be observed on the metal interface. The amount of metal removed by shock wave erosion is often used to measure the intensity of the cavitation. One also should add that other phenomena (production of free radicals, $H, OH, HO_2$, and toxic agents such as ozone or hydrogen peroxide) take place in a water cavitating field which can also contribute to the death of microorganisms. The denaturization of enzymes (Macleod R. M., Dunn F. J.; Acous. Soc. Am., vol. 42, no. 2:527–529, 1967) such as Trypsid, α-chymotrypsin, and Lactate dehydrogenase, has also been mentioned recently as an important factor to affect microorganism metabolisms.

It is apparent, however, that any process which will reduce the time necessary to decontaminate instruments or containers is most welcome in industry and any process which will accomplish this at a lower temperature will allow the use of a wider variety of materials from which said instruments or containers can be produced.

SUMMARY OF THE INVENTION

It is, therefore, an object of the present invention to provide a new method or pasteurizing, decontaminating or disinfecting, using the combined effect of both heat and ultrasonics on the liquid medium containing the objects.

A further object of the present invention is to decrease either the time required for pasteurization of objects or the temperature required to pasteurize said objects, or both.

It is a further object of the present invention to show that the ultrasonic irradiation of the hot water medium during equipment pasteurization can reduce the thermal death time (TDT) of the microorganisms and thus reduce the processing temperature while maintaining the same biocidal efficacy.

Another object of the present invention is to show that ultrasonic irradiation of the hot water medium during equipment pasteurization can affect the thermal death time (TDT) of the microorganisms to such an extent that at the 76.7° C. (170° F.) temperature, one can decrease the exposure time while maintaining the same biocidal efficacy.

A still further object of the present invention is to provide a process of treating objects in a liquid or aqueous medium with ultrasound below 150 KHz and heat.

Yet another object of the present invention is to provide a method of pasteurizing, disinfecting, or decontaminating objects in liquid or aqueous medium at temperatures or for periods of time less than that used in ordinary treatments.

These and other objects of the present invention will become apparent from the following detailed description and drawings, wherein:

FIG. 1 is a graph showing the preferred range for ultrasonic pasteurization; and FIG. 2 is a graph showing the synergistic action of ultrasonics in hot water pasteurization.

It has been found that the most ideal range for producing cavitation in liquids is below 150 KHz. It has further been found that this cavitation aids in heat disinfection of objects in aqueous mediums. It has further been found that the combination of heat and ultrasonics on aqueous disinfecting mediums is of a synergistic nature and results in more than the additive effect of both heat and ultrasound used separately. The aqueous medium can be water or water containing various surfactants.

The combination of the use of ultrasound with heat lowers the necessary temperature to which a solution has to be heated to pasteurize objects contained therein over the same period of time which would be required without the ultrasound, and if the same temperature is used both with or without ultrasound, the time required to produce the same amount of kill is reduced.

DETAILED DESCRIPTION OF THE INVENTION

As stated above, there has been found a new method of pasteurizing, disinfecting, or decontaminating the surfaces of medical, dental, surgical, food processing instruments or other objects in a liquid phase by placing the objects in the liquid and treating them with heat and ultrasonic radiation.

This method considerably reduces the time or temperature needed to kill non-sporulated bacteria, vegetative cells, fungi and viruses which contaminate surfaces, especially on hospital, medical, dental, and surgical instruments. Ultrasonic pasteurization also improves the cleanliness of instruments by a faster removal and disintegration of inert organic matter deposits. The method is compatible with the use of surfactants and detergents of the anionic, non-ionic, cationic and amphoteric type and can be performed in either a continuous or batch process. A particularly efficient biocidal combination consists of a mixture of anionic agents with small amounts of inorganic ionizable cation salts. Said ultrasonic pasteurizing method can also be used to continuously or batch process aqueous liquid suspensions such as food or pharmaceuticals.

In the method of the present invention, pasteurization is defined as a technique which will kill all pathogenic nonspore former bacteria, the hydrophilic and lipophilic viruses (with the exception of Virus Heptatitis B) and the vegetative forms of yeasts, fungi, and molds, which may contaminate anesthesia, respiratory therapy and urology equipment in normal hospital or medical practice.

To better understand the synergistic cidal effect of ultrasounds, combined with thermal energy, there will be described briefly how sonic and ultrasonic energy can greatly affect the viability of microorganisms in a liquid phase.

Although a little complex at first sight, the physical action of sonic or ultrasonic waves can be brought into play in four major ways: through large variations of pressure, motion, heat degradation, or electrical phenomena. Acoustic energy is carried through a liquid by the back and forth motion of the molecules along the direction of propagation. This produces alternate adiabatic compressions and rarefactions, together with corresponding changes in density and temperature.

Since there are periodic increases and decreases of the pressure in the liquid, it is undestandable that during the negative pressure phase, one may reach a point where we can overcome the natural cohesive forces of the liquid. Then a new phenomenon known as "cavitation" takes place. It corresponds to the formation followed by a rapid collapse of small cavities through the entire liquid. According to the energy density level, the cavities are filled with gas or vapor. In the latter case, their collapse produces very large amplitude shock waves (several atmospheres) with local temperatures up to a few hundred degrees centigrade or more. Electrical discharges are also believed to occur during the bubbles collapse (sonoluminescence effect).

For an equal acoustic energy density level in the liquid phase, one produces larger amplitude variations in the low frequency range (15 KHz to 150 KHz) than in the upper region of the ultrasonic spectrum. One also needs less energy to reach the "cavitation" threshold at the lower end of the ultrasonic spectrum. This is why the present invention is restricted to high energy insonation at frequencies below 150 KHz in the region where cavitation is maximized. When the frequency increases above 150 KHz, enormous amounts of energy are needed to reach the cavitation threshold. Syrotyuk (Sov. Acoust., vol. 8, no. 2:216–219, 1962), for instance, showed that intensity levels as high as 6,000 watts/cm$^2$ were needed to reach the cavitation threshold at 500 KHz. At still higher frequencies, it is even debated if true vaporous cavitation could be reached with very high densities of acoustic energy. The theoretical limit, above which cavitation cannot take place under normal conditions (water medium), was given as 10 MHz by Neppiras and Noltingk (Proc. Phys. Soc., 63 B, 9, 674–685, 1951). Other authors like Gaertner (J. Acoust. Soc. Am., 26:6, 977–980, 1951) place this limit around 2 MHz.

The present invention has been restricted to frequencies lower than 150 KHz because higher frequencies will correspond to a higher directivity of the transducer beam (Piston type Fraunhoffer diffraction effect) which will make it impossible to create a uniform field in a large tank of heated water or solvent. To apply the method of the present invention, one must create high intensity cavitating fields. This means that one must reach average intensities levels of 1 to 10 watts/cm$^2$ in degassed water. If converting these data into practical acoustic energy densities radiated per unit of volume, one can see that the process will be best practiced with energy densities of 15 to 55 watts per liter. The minimum average energy density should be comprised between 5 and 10 watts per liter of irradiated water or liquid phase.

An important factor behind the present invention is the well-known fact (see FIG. 1) that at low frequency in degassed water or aqueous solutions, the intensity of cavitation erosion peaks between 60° C. and 68° C. Further temperature increases correspond to a sharp decrease of cavitation shock wave intensity. This alone may explain why cavitation tremendously increases the cidal action of thermal pasteurization in the 60° C. to 68° C. temperature range. Only water or aqueous solutions seen to exhibit this peculiar behavior. The fact that the intensity of cavitation shock waves is reduced when the liquid temperature is higher than 68° C. is sometimes explained by an increase in solvent molecules inside cavitation bubbles. Such sudden increases could then prevent the complete collapse of the cavitation bubble. Although the 60° C. to 68° C. interval is by far the more economical and favorable range to observe the synergistic cidal action of ultrasonics in hot water solutions, one could also use lower temperature by increasing the density of acoustic energy.

The present invention has also many other advantages over the classical pasteurization in hot water alone. Ultrasonation enables a better dispersion of bacteria agglomerates, it also uncovers microorganisms wrapped inside mucus, proteins, blood, tissues, and inert matter. Respiratory therapy, anesthesia and urology equipment carry, in general, a light load in exogenous proteins, but in some cases microorganisms could be hidden in organic matter (mucus, blood serum, etc.), which is easily coagulated and hardened by heat. A poor precleaning without detergents can also leave organic residues containing pathogenic bacteria which may be more difficult to destroy (they deposit inside parts, etc.). The scrubbing action of cavitation shock waves will not only destroy the protein envelope to help kill bacteria faster, but will also provide cleaner interfaces in harder to clean components (corrugated tubings and small nebulizer parts, etc.).

The synergistic action of ultrasonics in hot water pasteurizing can be seen from the curves in FIG. 2. Since the TDT of *Staphylococcus aureus* corresponds to 30 minutes at 65.6° C. (150° F.), this microorganism was used to assess the influence of cavitating ultrasonics at 27 KHz with a density of acoustic energy on the order of 15 watts/liter. A microbial suspension containing $10^6$ organisms per cubic centimeter was placed in test tubes which were submerged in the water and removed at regular 10 minute intervals. The height of the suspension was at least equal to half a wave length. The temperature in the water or in the cavitating water bath was maintained constant ($\pm 1°$ C.) by recirculation through a refrigeration unit.

The method of cultivation consisted or agar slant transferred to 3% trypticase soy broth. It was incubated for 24 hours at 35° C. and centrifuged, and suspended in 0.9% NaCl solution again. One cubic centimeter samples were drawn at appropriate times and properly diluted. Each dilution was plated on a Petri dish utilizing nutrient agar as the growth medium (10 cc. diluted saline microbial suspension and 10 cc. 2% nutrient agar). The culture was then incubated 40 hours Curve A shows that the number of surviving microorganisms insonated at room temperature (25° C.) decreases very quickly during the first 60 minutes. From a few complementary tests done after 120 minutes, it appears that there is another slow down in the neighborhood of 120 minutes. This, of course, is in full agreement with other authors' observations since it has been well-established that the cidal efficacy of ultrasounds decreases sharply when the microorganisms concentration is extremely small. Another curve (not shown in FIG. 2) was drawn with *E. coli* bacteria and it exhibited the same decay shape.

Curve B shows the thermal death rate of the *S. aureus* when maintaining the water bath at 65.6° C. without any ultrasonic irradiation.

Curve C shows the killing rate of *S. aureus* when combining insonation in the cavitating ultrasonic field with a water temperature of 65.6° C. One can see that the influence of cavitating ultrasonic fields is more than a mere adding effect.

For instance, it could be said that the contribution of ultrasonics alone is a 2 logs decrease after 30 minutes. In this case, the end point of the pasteurizing curve B should be moved to 20 minutes to add the benefit of a 2 logs decrease. The end point of curve C is at 18 minutes showing that there is more than an adding effect. Of course, the proceeding reasoning is not even true if one considers that the ultrasonic death rate slows down after 60 minutes. This makes it more obvious that we deal with a synergistic cidal effect of ultrasonics.

Any decrease in temperature to achieve the type of disinfection requested for anesthesia, respiratory therapy and urology equipment is extremely important since it allows one to process a wider range of heat sensitive equipment while also minimizing the drawbacks of heat coagulation of proteins.

It is to be understood that various chemical additives could be added to the hot water without affecting the cidal efficacy of the ultrasonic pasteurizing method. For instance, various detergents and surface active agents of the cationic, anionic, non-ionic or amphoteric type could be added to promote a faster surface scrubbing under the twin action of cavitation and thermal energy. Additionally, traces of coloring agents or fragrances could also be used from a cosmetic viewpoint without interferring with the cidal process. Buffering agents such as phosphates, malates, citrates, carbonates, bicarbonates and the like salts can be used to adjust the pH of the water or aqueous solution without affecting the invention. It has previously been found that adding highly ionizable salts of mono or divalent cations of mineral and organic acids can boost the cidal process when added to anionic surfactants. Such a procedure did not adversely affect the efficacy of ultrasonic pasteurization and, in some instances, seemed to work to improve the safety margin of the method of the present invention.

As previously stated, ultrasonic pasteurization should not be used to destroy resistant pathogenic spores in their dormant state (*Cl. sporogenes, B. subtilis, Cl. tetani, Cl. perfringens, Cl. botulinum*, etc.). It was, however, noted that under the double action of cavitation shock waves and heat (especially in the presence of small amounts of acid-anionic surfactants), the resistance of *B. subtilis* spores to subsequent heat sterilization is greatly decreased. One could speculate that hot water helps to change the spore into its vegetative state, thus enabling ultrasonic pasteurization to act as a "heat shock" treatment.

EXAMPLES

The following are examples for the purpose of illustration of the invention and it should be understood that they should not be construed as limiting the invention to the details given.

TABLE I

IMPROVEMENTS OF THERMAL DEATH TIMES WITH ULTRASONIC IRRADIATION

Ultrasonic Field: Nominal Frequency 27 kHz
Acoustic Energy Density: 15 watts/liter
Medium of Dispersion: Potable Water (Federal Standards)
Microorganism Concentration: $10^5$ to $10^6$ per cubic centimeter.
Standard Hot Water Pasteurization in Hospitals Corresponds to a 30 Minutes Exposure at 76.7° C.

| Type of Microorganisms | Killing Time With Ultrasonics in Hot Water | Killing Time in Hot Water Alone | Reduction of Processing Time |
|---|---|---|---|
| *Mycobacterium tuberculosis* | 15 min. at 60° C. | 20 min. at 60° C. | 25% |
| *Diplococcus pneumoniae* | 5 min. at 54.4° C. | 10 min. at 54.4° C. | 50% |
| *Streptococcus pyogenes* | 20 min. at 63° C. | 30 min. at 63° C. | 33.3% |
| *Str. faecalis* | 3 min. at 65.6° C. | 5 min. at 65.6° C. | 40% |
| *Staphylococcus aureus* | 18 min. at 65.6° C. | 30 min. at 65.6° C. | 40% |
| *Cornybacterium diphtheriae* | ½ min. at 60° C. | 1 min. at 60° C. | 50% |
| *Salmonella typhi* | 1 min. at 60° C. | 2 min. at 60° C. | 50% |
| *Escherichia coli* | 1 min. 60°65.6° C. | 2 min. at 65.6° C. | 50% |
| *Klebsiella pneumoniae* | 1 min. at 65.6° C. | 2 min. at 65.6° C. | 50% |
| *Proteus vulgaris* | 1 min. at 65.6° C. | 2 min. at 65.6° C. | 50% |
| *Pseudomonas aeruginosa* | 1 min. at 65.6° C. | 2 min. at 65.6°C. | 50% |
| Fungi | | | |
| *Trichophyton mentagrophytes* | 20 min. at 63° C. | 30 min. at 63° C. | 33.3% |
| Viruses | | | |
| Hydrophilic - Echo - 25 | 20 min. at 60° C. | 30 min. at 60° C. | 33.3% |
| Lipophilic - Herpes simplex | 20 min. at 60° C. | 30 min. at 60° C. | 33.3% |

TABLE II

TEMPERATURE LOWERING WITH ULTRASONIC IRRADIATION

Ultrasonic Field: Nominal Frequency 27 kHz
Acoustic Energy Density: 15 watts/liter
Medium of Dispersion: Potable Water (Federal Standards)
Microorganism Concentration: $10^5$ to $10^6$ per cubic centimeter
Standard Hot Water Pasteurization in Hospitals Corresponds to a 30 Minute Exposure at 76.7° C.

| Type of Microorganisms | Killing Time-Temperature with Ultrasonics in Hot Water | Killing Time-Temperature in Hot Water Alone | Reduction of Temperature |
|---|---|---|---|
| Bacteria | | | |
| *Diplococcus pneumoniae* | 10 min. at 48° C. | 10 min. at 54.4° C. | 6.4° C. |
| *Proteus vulgaris* | 2 min. at 58° C. | 2 min. at 65.5° C. | 7.6° C. |
| *Pseudomona aeruginosa* | 2 min. at 58° C. | 2 min. at 65.5° C. | 7.6° C. |
| *Klebsiella pneumoniae* | 2 min. at 58° C. | 2 min. at 65.5° C. | 7.6° C. |
| *Escherichia coli* | 2 min. at 58° C. | 2 min. at 65.5° C. | 7.6° C. |
| *Staphylococcus aureus* | 30 min. at 58° C. | 30 min. at 65.5° C. | 7.6° C. |
| *Streptococcus pyogenes* | 30 min. at 57° C. | 30 min. at 63° C. | 6° C. |
| *Str. faecalis* | 5 min. at 58° C. | 5 min. at 65.5° C. | 7.6° C. |
| *Mycobacterium tuberculosis* | 20 min. at 55° C. | 20 min. at 60° C. | 5° C. |
| Fungi | | | |
| *Candida albicans* | 30 min. at 57° C. | 30 min. at 68° C. | 6° C. |
| Viruses | | | |
| Lipophilic: Influenza $A_2$ | 30 min. at 53° C. | 30 min. at 60° C. | 7° C. |
| Hydrophylic: Polio Virus Type I | 30 min. at 53° C. | 30 min. at 60° C. | 7° C. |

TABLE III

INFLUENCE OF ADDITIVES AND ACOUSTIC FIELDS ON ULTRASONIC PASTEURIZATION

Microorganism: Staphylococcus aureus
Medium of Dispersion: Potable Water (Federal Standards)
Standard Hot Water Pasteurization in Hospitals Corresponds to a 30 Minute Exposure at 76.7° C.

| Additives | Killing Time-Temperature with Additive & ultrasonics in Hot Water | Killing Time-Temperature with Ultrasonics in Hot Water | Emission Frequency | Acoustic Energy Density |
|---|---|---|---|---|
| $C_{12}$ ABS* (0.05% w/w) + NaCl (0.15% w/w) | 15 min. at 65.6°C. | 18 min. at 65.6° C. | 27 kHz | 15 watts/liter |
| $C_{12}$ ABS (0.05% w/w) + KCl | 15 min. at 65.6° C. | 18 min. at 65.6° C. | 27 kHz | 15 watts/liter |
| $C_{12}$ ABS (0.05% w/w) + LiCl | 15 min. at 65.6° C. | 18 min. at 65.6°C. | 27 kHz | 5 watts/liter |
| $C_{12}$ ABS (0.05% w/w) + $MgCl_2$ | 15 min. at 65.6° C. | 18 min. at 65.6° C. | 27 kHz | 45 watts/liter |
| $C_{12}$ ABS (0.05% w/w) + $NaHCO_3$ | 15 min. at 65.6° C. | 18 min. at 65.6° C. | 27 kHz | 10 watts/liter |
| $C_{12}$ ABS (0.05% w/w) | 16 min. at 65.6° C. | 18 min. at 65.6° C. | 27 kHz | 15 watts/liter |
| Non ionic: TRITON X 100 Alkyl phenoxy polyethoxy ethanol (0.25% w/w) | 18 min. at 65.6° C. | 18 min. at 65.6° C. | 10 kHz | 5 watts/liter |

TABLE III-continued
INFLUENCE OF ADDITIVES AND ACOUSTIC FIELDS ON ULTRASONIC PASTEURIZATION Microorganism: Staphylococcus aureus
Medium of Dispersion: Potable Water (Federal Standards)
Standard Hot Water Pasteurization in Hospitals Corresponds to a 30 Minute Exposure at 76.7° C.

| Additives | Killing Time-Temperature with Additive & ultrasonics in Hot Water | Killing Time-Temperature with Ultrasonics in Hot Water | Emission Frequency | Acoustic Energy Density |
|---|---|---|---|---|
| Anionic: SLS | | | | |
| Sodium Lauryl sulfate (0.25% w/w) | 18 min. at 65.6° C. | 18 min. at 65.6° C. | 27 kHz | 5 watts/liter |
| Cationic: CAT | | | | |
| Cetylpyridinium chloride (0.5% w/w) | 18 min. at 65.6° C. | 18 min. at 65.6° C. | 55 kHz | 5 watts/liter |
| Ampholytic: DERIPHAT 160 (0.05% w/w) | | | | |
| Di sodium N-lauryl B imino-dipropionate | 18 min. at 65.6° C. | 18 min. at 65.6° C. | 120 kHz | 5 watts/liter |

*Anionic alkyl benzene sulfonate in which the alkyl is a branched chain dodecyl group composed of four propylene units.

Table I shows how the exposure time of the standard thermal death times can be reduced to achieve complete microorganism destruction when combining ultrasonic irradiation with hot water treatment. A time reduction comprised between 25 and 50% is the result of ultrasonic pasteurization in a cavitating aqueous solution.

Table II shows how much one can also reduce the critical killing temperature when maintaining the same exposure time as the one agreed upon for the classical thermal death time (TDT). An average lowering close to 8° C. does not seem to affect the cidal efficacy for bacteria, pathogenic fungi and viruses.

This means that the current operating conditions (30 minutes at 76.6° C.) used in hospitals for decontaminating anesthesia, respiratory therapy and urology equipment could be lowered to a 30 minute exposure in the neighborhood of 68° C. which corresponds to the upper temperature limit for maximizing cavitation intensity. Such a lowering of the temperature will minimize evaportion rates while increasing the safety margin for processing many highly heat sensitive plastic instruments and devices.

Table III confirms the fact that adding small amounts of various surfactants does not decrease the efficacy of the method. It also shows that adding certain mono and divalent cations of ionizable salts can even improve the efficacy of ultrasonic pasteurization in the presence of anionic surfactants.

All the tests were conducted in agreement with the methods described in the 12th edition of the "Methods of Analysis of the Association of Official Analytical Chemists" (1975 ed.).

Although several specific examples of the inventive concept have been described for purposes of illustration, the invention should not be construed as limited thereby nor to the specific features mentioned therein, except as the same may be included in the claims appended hereto. It is also understood that changes, modifications, and variations may be made without departing from the spirit and scope of the invention.

For instance, it is obvious that the method of the present invention can also be used to pasteurize continuously or in batches, liquids or liquid dispersions (fruit juices, baby foods, milk, pharmaceuticals, etc.) containing microorganisms. The synergistic action of ultrasonics, combined with thermal energy will result in a microbial decontamination as long as said contaminated liquid will remain exposed to both forms of energy according to the experimental conditions hereabove described.

I claim:

1. A method for pasteurizing, decontaminating, or disinfecting medical, dental, and surgical instruments or other objects in liquid phase without the use of chemosterilants consisting essentially of placing said objects in a hot aqueous solution at a temperature of from 58° to 68° C. for a time of from about 15 to 20 minutes while creating at the same time an ultrasonic field having an acoustic energy density from about 5 to about 55 watts per liter and an ultrasonic frequency below about 150 kHz in said aqueous non-chemosterilant solution.

2. The method of claim 1 wherein the nominal frequencies of the ultrasonic emission are between 15 KHz and 55 KHz.

3. The method of claim 1 wherein the acoustic energy radiated throughout the hot aqueous phase is higher than 15 watts per liter.

4. The method of claim 1 wherein the aqueous phase is at a temperature of from 58° to 63° C. and said instruments are exposed to an ultrasonic field at said temperature for about 20 minutes.

5. The method of claim 1 wherein the instruments are processed in a continuous manner by a combination of ultrasonic cavitation and exogenous thermal energy.

6. The method of claim 1 wherein the instruments are processed in a batch manner by a combination of ultrasonic cavitation and exogenous thermal energy.

7. The method of claim 1 wherein surface active agents are added to the hot aqueous phase, said surfactants being selected from a group consisting of non-ionic, anionic, cathionic, and amphoteric detergents.

8. The method of claim 7 wherein the amount of said detergents are 0.05% to 5% by weight.

9. The method of claim 1 wherein ananionic agent of the alkyl benzene sulfonate type is added to the hot aqueous phase at a concentration of between 0.05% and 0.5% by weight.

10. The method of claims 1 or 9 wherein at least one member of the group consisting of ionizable salts of mono and divalent cations, alkaline earths and metals of Group IIB of the periodic table, is added at a minimum concentration of 0.05% by weight.

* * * * *